United States Patent [19]
Ishibashi et al.

[11] Patent Number: 5,532,488
[45] Date of Patent: Jul. 2, 1996

[54] APPARATUS AND METHOD FOR EVALUATING ORIENTATION FILM

[75] Inventors: Mitsuru Ishibashi, Chiba-ken; Hideyuki Sasaki, Kanagawa-ken; Tatsuo Nomaki, Kanagawa-ken; Akira Tanaka, Kanagawa-ken; Rei Hasegawa, Kanagawa-ken, all of Japan

[73] Assignee: Kabushiki Kaisha Toshiba, Kawasaki, Japan

[21] Appl. No.: 305,905

[22] Filed: Sep. 13, 1994

[30] Foreign Application Priority Data

| Sep. 13, 1993 | [JP] | Japan | 5-227072 |
| Sep. 14, 1993 | [JP] | Japan | 5-228465 |
| Dec. 29, 1993 | [JP] | Japan | 5-353763 |

[51] Int. Cl.$^6$ .................................................. G01J 4/00
[52] U.S. Cl. .................................. 250/341.3; 250/341.8; 250/347
[58] Field of Search .................. 250/341.3, 347, 250/341.8

[56] References Cited

U.S. PATENT DOCUMENTS

| 4,446,719 | 5/1984 | Lambert | 250/341.8 |
| 4,631,408 | 12/1986 | Zelmanovic et al. | 250/341.3 |
| 4,654,529 | 3/1987 | Boulay et al. | 250/341.3 |
| 5,365,067 | 11/1994 | Cole et al. | 250/341.3 |

FOREIGN PATENT DOCUMENTS

| 60-117119 | 6/1985 | Japan | 250/341.3 |
| 64-35419 | 2/1989 | Japan . | |
| 64-35418 | 2/1989 | Japan . | |
| 4-95845 | 3/1992 | Japan . | |

*Primary Examiner*—Constantine Hannaher
*Assistant Examiner*—Virgil O. Tyler
*Attorney, Agent, or Firm*—Foley & Lardner

[57] ABSTRACT

An orientation film evaluating apparatus and a rubbing processing apparatus by which the orientation capability for a liquid crystal orientation film can be measured quantitatively with high sensitivity and accuracy even during an actual production process, and an orientation condition is controlled precisely so as to obtain a stable production condition and to improve productivity and yield therefor. The orientation film evaluating apparatus includes: a unit for radiating infrared light; a polarizing portion which polarizes the infrared at varied angles to an orientation film, and for irradiating the polarized infrared lights to the orientation film; a detection portion which detects infrared light reflected upon the orientation film; and an evaluating portion which obtains a difference of absorbance of infrared light detected by the detection portion with respect to a polarized direction of the orientation film, and which evaluates an orientation capability of the orientation film.

11 Claims, 13 Drawing Sheets

TILT ANGLE (DEGREE)

APPARATUS AND METHOD FOR EVALUATING ORIENTATION FILM

BACKGROUND OF THE INVENTION

1. Technical Field

The present invention relates to an orientation capability evaluating apparatus which evaluates orientation capability of an orientation film used for liquid crystal display elements.

2. Background Art

In recent years, liquid crystal displays have been in wide-spread use. In the liquid crystals used in a liquid crystal display element constituting the liquid crystal display apparatus, its orientation process is an indispensable technique. It becomes known that a state of the orientation processing is responsible for change in a display quality and a display error.

The recent study of the orientation mechanism has lead to research for realizing optimization of the state of the orientation.

As an alignment processing method or an orientation processing method, almost all of the currently-used liquid crystal elements utilize a substrate on which the orientation processing is perfomed, thereby, the orientation of liquid crystal molecules is controlled. In this specification, the terms orientation and alignment will be used interchangeably. As the orientation processing method for the substrate, the surface of polymer film is rubbed unidirectionally by rubbing cloth such as polyester cloth, and there is obtained the orientation film by properly processing so that an orientation vector thereof is oriented in a predetermined direction.

The above-mentioned method for rubbing the orientation film is suitable for mass production and is less costly, so that most of the liquid crystal display elements utilize the orientation film made in this method. However, though the procedure in the rubbing technique is rather simple, its decision making on a produdction basis is very difficult. In other words, the liquid crystal molecular orientation capability greatly changes depending on orientation film material, rubbing material, the number of rubbing operations, rubbing speed and so on. Thus, it is not easy to achieve a stable rubbing operation.

The liquid crystal molecular orientation capability for the substrate can not be evaluated until after the liquid crystal display element is actually assembled utilizing the substrate on which the rubbing techinique is performed, and then its display characteristic is tested, in the conventional practice.

In Japanese KOKAI 64-35419, tried is the orientation capability evaluation by absorbance utilizing linearly polarized infrared light. However, in this evaluation method, the glass absorbs the infrared light, so that measurement can not be carried out in a finished product utilizing a glass substrate. Therefore, it is necessary to make an orientation film by utilizing a test-purpose substrate such as calcium fluoride that transmits the infrared. The finished product means a commodity produced after a patterning process. In other words, a dummy or a test sample must be used in order for the evaluation purpose in the conventional practice.

Moreover, the direction of the sample substrate need be changed in order to change a polarizing direction, and the measurement is carried out through a polarizer. Thus, it is difficult or almost impossible to evaluate the orientation film during the production process.

Accordingly, even though there occurs a rubbing defect of the orientation film during the production process of the liquid crystal display elements in a factory line, such defect can not be found until the liquid crystal display is actually assembled, thus causing to deteriorate a production yield. Moreover, it is difficult to decide on a definite condition for rubbing, so that it is difficult to obtain the orientation film whose orientation is stable.

SUMMARY OF THE INVENTION

In view of the foregoing drawbacks, it is therefore an object of the present invention to provide an orientation film evaluating apparatus by which the orientation capability for the liquid crystal orientation film can be measured quantitatively with high sensitivity and accuracy even during an actual production process.

Another object of-the present invention is to provide an orientation film evaluating apparatus capable of evaluating a tilted angle of a polymer chain of a rubbing-processed orientation film.

Still another object of the present invention is to provide a rubbing processing apparatus capable of controlling precisely an orientation condition so as to obtain a stable production condition and to improve productivity and yield therefor.

According to one aspect of the present invention, there is provided an orientation film evaluating apparatus comprising: means for radiating infrared light; polarizing means for polarizing the infrared light at varied angles to an orientation film, and for irradiating the polarized infrared lights to the orientation film; detection means for detecting infrared light reflected upon the orientation film; and evaluating means for obtaining a difference of absorbance of infrared light detected by the detection means with respect to a polarized direction of the orientation film, and evaluating an orientation capability of the orientation film.

According to another aspect of the present invention there is provided an orientation film evaluating apparatus for a liquid crystal orientation film, comprising: means for radiating infrared light toward a rubbing-processed orientation film sample; measuring means in which the infrared light which is in a polarized state parallel to a plane formed by a rubbing direction of the orientation film sample and a direction normal to the surface of the orientation film sample is entered at various angles from the direction normal to the sample surface, at a characteristic absorption wavelength thereof; detection means for detecting the infrared light transmitted through the measuring means; and evaluating means for evaluating the orientation film based on a difference between the transmitted light obtained from the detection means at various angles.

According to still another aspect of the present invention, there is provided a rubbing processing apparatus which makes unidirectional a molecular orientation in the surface of a polymer orientation film formed on a substrate, comprising: rubbing means for rubbing the surface of the polymer orientation film at a unidirection; detection means for detecting a temperature of the surface of the polymer orientation film which is rubbing-processed by the rubbing means; and control means for varying a rubbing condition responsive to the temperature of the surface of the polymer orientation film detected by the detection means, wherein the controlling means sets the temperature of the polymer orientation film in a region to be rubbing-processed, in a range that is equal to or greater than a glass transition temperature for a polymer material constituting the polymer orientation film, and is within 60° from the glass transition temperature.

One advantage of the present invention is that it provides for the apparatus by which the orientation of the orientation film can be quantitatively measured with a high sensitivity and accuracy.

Another advantage of the present invention is that the rubbing-processed orientation film is properly evaluated even in view of the tilted angle of a polymer chain of the rubbing-processed orientation film.

Still another advantage of the present invention is that the orientation state is further precisely controlled so as to obtain the stable production condition and increase the productivity and yield for producing the liquid crystal orientation film, so that an economically priced and highly precise liquid crystal display unit presenting a highly qualified image is produced.

BRIEF DESCRIPTION OF THE DRAWINGS

These and other objects, features and advantages of the present invention will become more apparent from the following description of the preferred embodiment taken in conjunction with the accompanying drawings, in which:

FIG. 18 shows a top view of the sample substrate 6 and the mask 5 shown in FIG. 19.

DETAILED DESCRIPTION OF THE PREFERRED EMBODIMENTS

Figure 1:
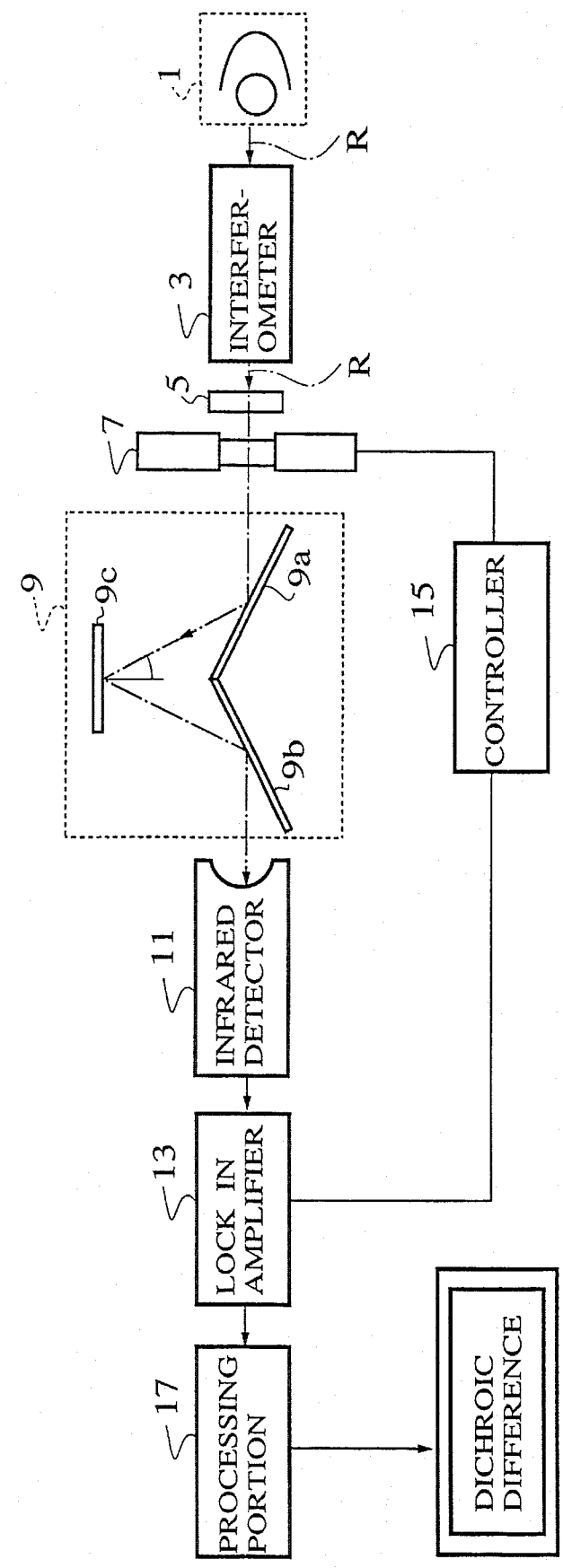
FIG. 1 is a block diagram showing the orientation film evaluating apparatus according to the first embodiment.

Features of the present invention will become apparent in the course of the following description of exemplary embodiments which are given for illustration of the invention and are not intended to be limiting thereof. Embodiments of the present invention will now be described with reference to the drawings.

FEATURE OF THE PRESENT INVENTION

By measuring an infrared dichroic difference that is a difference of absorbance obtained when reflected are the infrared lights of two linearly polarized lights which are perpendicular to each other, the orientation capability is evaluated. For example, the two linearly polarized lights are switched at a high speed by a photoelastic modulator and a lock-in amplifier, so as to consecutively measure the infrared dichroic difference. The linear polarization is adjusted preferably at approximately 45° with respect to a plane of incidence toward a sample. Moreover, by taking adjustment with respect to a film thickness of the orientation film calculated from a value of the absorbance, the liquid crystal molecular orientation capability of the orientation film is measured with a high sensitivity and accuracy. Moreover, an apparatus realizing the infrared dichroic difference can be implemented during the production line of the liquid crystal display elements.

BASIC CONCEPT

First, a basic concept in the present invention will be described in detail.

As for a mechanism in which the liquid crystal molecules are aligned by the orientation film that is rubbing-processed, it is considered that a polymer chain in the orientation film is oriented in a predetermined direction, so that the liquid crystal molecules are thus oriented by interaction with the orientation film molecules. Therefore, in order to determine the liquid crystal orientation capability of the orientation film, a molecular orientation for the orientation film per se shall be examined. However, there has not been available a method for measuring the molecule orientation with high precision, in the conventional practice.

Now, in the present invention, the molecular orientation degree is investigated by a difference of absorbance obtained when reflected are the infrared lights of two linearly polarized lights which are perpendicular to each other.

In a system for measuring the infrared dichroic difference, by utilizing the photoelastic modulator, two linearly polarized lights each of which is perpendicular to other, can be switched at a high speed of a hundred and some tens of kHz. Note that water vapor and carbon dioxide gas in the air in the infrared dichroic difference measuring system absorbs the infrared light, and its state constantly changes. Thus, if the absorbance measurement for the two linearly polarized lights that are perpendicular to each other are separately performed, the water vapor or carbon dioxide gas may be negatively affected at the time the difference of the two absorbances is taken.

Then, the value of the dichroic difference in the orientation of the orientation film molecules is rather small, so that the influence of the water vapor and carbon dioxide gas can not be neglected. Thus, the two linearly polarized lights are perpendicular to each other are switched at the high speed. Thus, the almost simultaneous two absorbance difference is obatained, so as to minimize the influence of the water vapor and carbon dioxide gas, thus realizing the measurement with high sensitivity and accuracy.

Next, let us consider the influence of a polarization characteristic in the measuring system. There exists the polarization characteristic in a mirror used in the measuring system such as a spectrometer or spectroscope, and reflectance thereof differs depending on a polarizing direction. The value of the dichroic difference caused by the orientation of the orientation film molecules under such a polarization characteristic, is rather small, so that the influence of the polarization property can not be neglected. In order to avoid this polarization characteristic, the linearly polarized light direction for the infrared light is set to 45° against the plane of incidence of the infrared light toward the sample; the plane of the incidence indicates a plane that the incident light and the reflected light pass. Thereby, the two polarized lights used for the measurement becomes symmetrically ±45° against the mirror in the measuring system, so that the difference of the reflectance due to the polarization characteristic is not caused.

Moreover, in the sample itself, the reflectance of its substrate presents the polarization characteristic in the case of measuring the reflection, so that the polarization characteristic can be eliminated by measuring at the above angles. It is also necessary to perform a fine adjustment of the angle in the vicinity of 45° so that the polarization characteristic completely disappears.

The dichroic difference of the infrared absorbance in the orientation film changes greatly depending on the film thickness of the orientation film. Therefore, correction is necessary to correct the fluctuation of the dichroic difference due to a change in the film thickness. Such a technique concerning the correction will be described below.

It is known that when the infrared light is reflected on the metal surface there is caused a standing wave on the surface. When the incidence angle $\theta_1$ is sufficiently small, x and y components of electric field vector are expressed as functions of distance z from the surface, respectively, in equation (1).

$$E_x = -2A_x\{\sin(2\pi n_i z/\lambda)\}e^{\hat{}}(-i(\omega t - \pi/2)) \quad (1)$$
$$E_y = -2A_y\{\sin(2\pi n_i z/\lambda)\}e^{\hat{}}(-i(\omega t - \pi/2)),$$

indicates power to (e), where $A_x$ and $A_y$ indicates maximum amplitudes for x and y components for the electric vector of the standing wave, respectively; $n_1$ is an index of refraction for transparent medium; $\lambda$ is a wavelength of the incident light; and an exponent portion indicates a time changes at angular frequency of $\omega$. The absorption strength of the infrared light is proportional to a frequency electric field intensity $E^2$ of the standing wave (see equation (2)).

$$E^2 = C \cdot \sin^2 x, \quad (2)$$

where $x = 2\pi n_1 z/\lambda$, and C is some constant.

Figure 2:
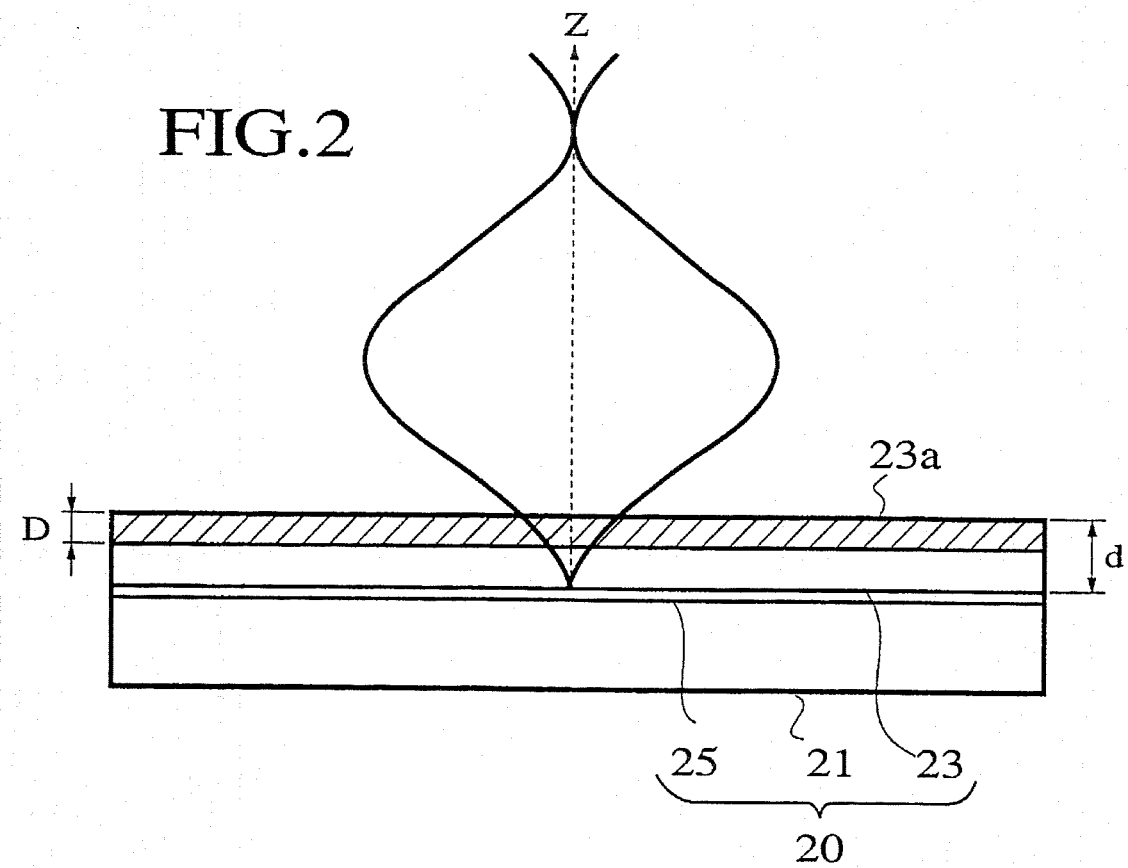
FIG. 2 shows structure of the liquid crystal orientation film.

FIG. 2 shows structure of the liquid crystal orientation film. Referring to FIG. 2, in an orientation film substrate 20, an ITO film 25 (indium tin oxide) that is $In_2O_3$:Sn film, is formed on a glass substrate 21. An orientation film 23 such as polyimide is formed on the surface of the IT0 film 25. On the surface 23a of the orientation film 23, there is formed an orientation layer along which the alignment is performed by rubbing at depth of D against the film thickness d of the orientation film.

Then, when the film thickness d varies, the electric field strength in which the film is aligned, is also changed. Thus, even though there is no change in the rubbing depth D, the infrared absorbing intensity and dichroic difference are changed in accordance with an integration of equation (2) representing the electric field strength, as shown below.

Suppose that the infrared absorbance according to a transmission method is denoted as At, and the infrared difference is denoted as $\Delta A_t$.

$$\Delta A_t = (\alpha_{para} - \alpha_{vert})(d - (d - D)) \quad (3)$$
$$= (\alpha_{para} - \alpha_{vert})D$$
$$A_t = (\alpha_{para} + \alpha_{vert})d \quad (4)$$

where $\alpha_{para}$ and $\alpha_{vert}$ correspond to infrared's absorption coefficients when parallel to and vertical to the rubbing direction, respectively; the infrared's absorption coefficient changes depending on the wavelength of the infrared.

On the other hand, integration of equation (2) representing the electric field strength is performed in the case of the reflection method. Thus, the infrared absorbance $A_t$ and the infrared dichroic difference $\Delta A_t$ are expressed by following equations (5) and (6).

$$\Delta A_t = (\alpha_{para} - \alpha_{vert})\int_{K-L}^{k} C\sin^2 x\, dx \quad (5)$$
$$= (\alpha_{para} - \alpha_{vert})C\{-(1/4)\sin 2K + (1/4)\sin 2(K-L) + (1/2)L\}$$

$$A_t = (\alpha_{para} + \alpha_{vert})\int_{o}^{K} C\sin^2 x\, dx \quad (6)$$
$$= (\alpha_{para} + \alpha_{vert})C\{-(1/4)\sin 2K + (1/2)K\}$$

where, $K = 2\pi n_i d/\lambda$ and $L = 2\pi n_i D/\lambda$

From these equations, the correction can be carried out to eliminate the influence of the film thickness in the measurement of the rubbing strength by means of the dichroic difference according to the reflection method.

EMBODIMENT NO. 1

Referring to FIG. 1, the first embodiment based on the basic concept will be described. FIG. 1 is a block diagram showing the orientation film evaluating apparatus according to the first embodiment.

Referring to FIG. 1, along an optical axis of an infrared, red light source 1, there are provided a Michelson interferometer 3, a polarizer 5, a photoelastic modulator 7, a reflection measuring unit 9 and an infrared detector 11. An lock-in amplifier 13 is connected to the infrared detector 11. The lock-in amplifier 13 is connected to a controller 15 and a processing portion 17. From the processing portion 17, a signal corresponding to the dichroic difference is output. The lock-in amplifier and the photoelastic modulator 7 are controlled by the controller 15 in a synchronous manner.

The orientation film is formed on an ITO vapor deposition glass substrate 20 (see FIG. 2) by utilizing a polyimide resin. After the orientation film is alignment-processed by a rubbing machine, the orientation evaluation is carried out by measuring the infrared dichroic difference thereof.

Next, an operation of the evaluating apparatus will be described along with measurement procedures.

An infrared light R radiated from the infrared light source 1 enters into the Michelson interferometer 3 which serves as a Fourier transform infrared spectrometer. After passing through the interferometer 3, the infrared light R is given a polarization modulation of, for example, 147 kHZ, by the polarizer 5 and the photoelastic modulator 7. In this embodiment, the infrared light R enters at an incidence angle of 30° with respect to the orientation film substrate, and is reflected at an angle of 45° with respect to the orientation direction 37 (FIG. 3) of the orientation film molecules, by the reflection measuring unit 9. This is illustrated in FIG.

Figure 3:
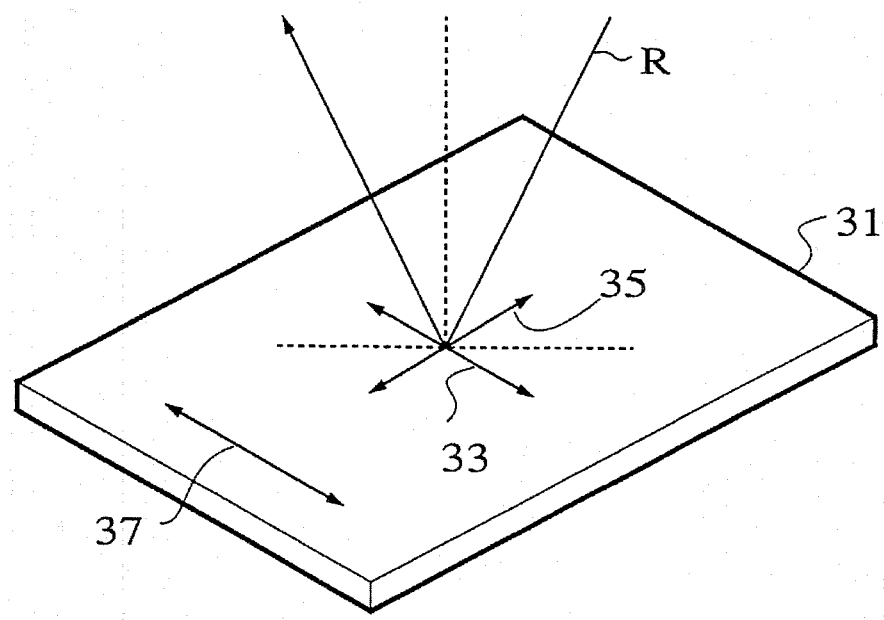
FIG. 3 illustrates a reflection state of the infrared light on the orientation film substrate.

FIG. 3 illustrates a reflection state of the infrared light on the orientation film substrate. The angles of both the polarizer 5 and the photoelastic modulator 7 are adjusted so that, on the orientation film substrate 31, two linearly polarlized lights 33, 35 that are orthogonal to each other on the sample surface are set at 0° and 90° with respect to the orientation direction 37. Referring to FIG. 2, the infrared light R is reflected by the ITO film 25 interposed by the polyimide film 23 and the glass substrate 21.

The reflected infrared light R having information on absorption of the polyimide orientation film 23a is converted to an electric signal by the infrared detector 11. The converted electric signal is set free from the polarization modulation by the lock-in amplifier 13 that is made synchronous with the photoelastic modulator 7 by the controller 15. At this stage, the signal corresponding to the infrared absorption is expressed in the form of the infrared dichroic difference due to the two linearly polarized lights. This signal is data-processed in the processing portion 17, and is given a division process by a background of the spectrum. Thereafter, the correction is performed against the film thickness d.

As for a correction equation, by equations (3)–(6), there is obtained the following equation (7) in terms of converting to the infrared dichroic difference $\Delta A_r$, $$\Delta A_r = C'(\Delta A_r/A_r) \cdot D \cdot \{(\sin 2K - 2K)/(\sin 2K - \sin 2(K-L) - 2L)\} \quad (7)$$

Evident from equation (7), there remain terms D and d in the event that $\Delta A_r$ is divided by $A_r$. Thus, the correction can not be carried out without knowing values of D and d. As for a value of the film thickness d, since the absorbance $A_r$ due to the reflection depends only on the film thickness d, the correction value can be known from the absorbance $A_r$ by observing correlation between the film thickness d and the absorbance $A_r$, so as to obtain beforehand an analytical curve thereof.

As for D, it is very difficult to obtain the rubbing depth from actual experiments. Thus, the rubbing depth D was corrected in a manner that a change of $\Delta A_r$ against the film thickness d becomes minimal.

As a result of the above measurements, the dependency of the film thickness in the infrared dichroic difference can be eliminated, and a coefficient of variation for the correction value was 4.7%.

Though the infrared light R enters at the incidence angle of 30° in the above exemplary embodiment, it shall be appreciated that the incidence angle may be 0° and the substrate may be rotated by 90°.

Moreover, though the ITO evaporation glass is used as the substrate in the above example, the substrate is not only limited thereto. There may be used anything on which formed is a film disposed at an orientation-film forming side, such as metal film, having a characteristic of reflecting the infrared light.

EMBODIMENT NO. 2

Figure 4A:
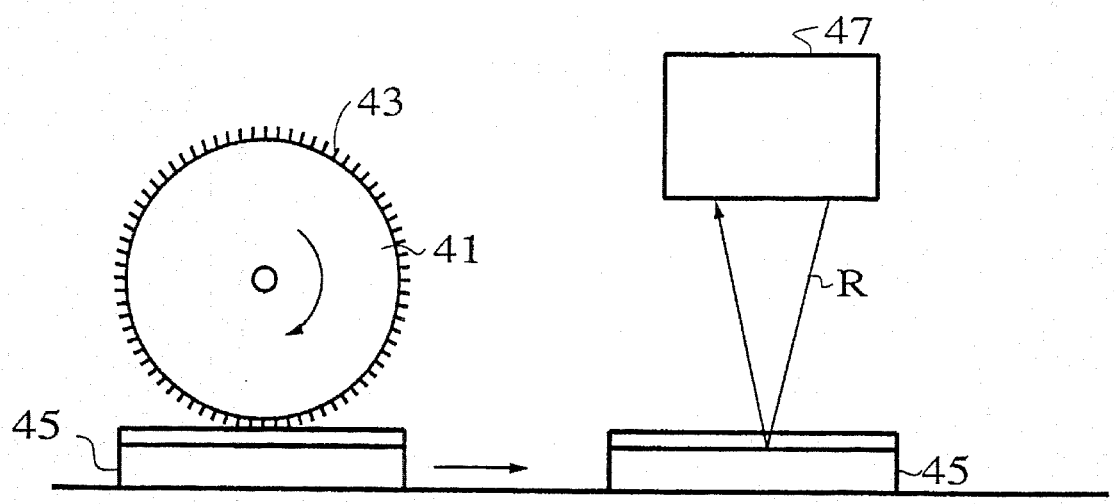
FIG. 4A and FIG. 4B illustrate the second embodiment where the evaluating apparatus is implemented to the production line of the liquid crystal panels.
Figure 4B:
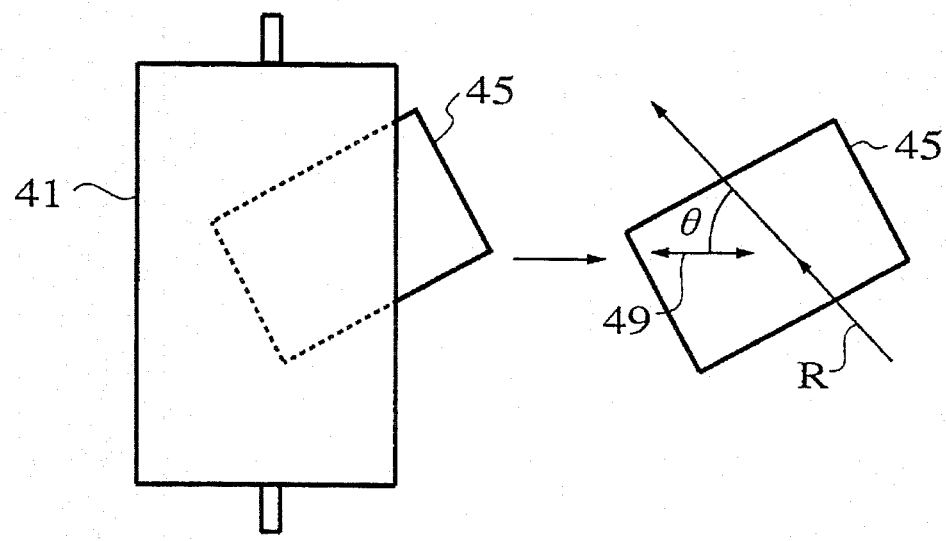

Referring to FIGS. 4A and 4B, the second embodiment based on the basic concept will be described.

It is to be noted that the present invention may be implemented on the production line of the liquid crystal orientation film. FIG. 4A and FIG. 4B illustrate the second embodiment where the evaluating apparatus is implemented on the production line of the liquid crystal panels.

Referring to FIG. 4A, a rubbing roller 41 is of a cylindrical shape. A rubbing cloth 48 is wrapped and wound around the outer circumferential surface of the rubbing roller 41. An orientation film substrate 45 is translated in the direction opposite to the rotation of the rubbing roller 41, thereby, the rubbing of the orientation film substrate 45 is carried out by the rubbing cloth 43. After the orientation film substrate 45 is alignment-processed by the rubbing roller 43, the orientation film substrate 45 is set below an orientation measuring apparatus 47. The orientation measuring apparatus 47 may have a similar structure describe in the first embodiment.

Referring to FIG. 4B, by using this orientation measuring apparatus 47, the infrared R is entered from the direction of θ, that is 45°, indicated in FIG. 4B with repect to an orientation direction 49 and is reflected. It shall be appreciated that the alignment process may be performed in a manner that the rubbing roller 43 is translated instead of moving the orientation substrate 45, so that a desirable translation without being affected by the vibration or the like can be realized to further improve accuracy of the orientation measurement. Moreover, as for the orientation film substrate 45 which presents a lower value than a predetermined infrared dichroic difference, the rubbing was performed again, so that a desirable rubbing strength was obtained.

Moreover, in addition to the number of the rubbing, other rubbing conditions can be automatically controlled in terms of a single condition or entire conditions integrally considered, so as to obtain a stable rubbing strength. The other rubbing conditions include a rotation speed of the rubbing roller, a translating speed of the substrate (or the translating speed of the rubbing roller), a depression degree of the rubbing roller and the surface temperature of the polyimide film.

As described above, the orientation capability of the liquid crystal orientation film can be quantitatively measured with high sensitivity and accuracy, even during the actual manufacturing line.

In summary, by employing the first and second embodiments, the orientation of the orientation film can be quantitatively measured with a high sensitivity and accuracy.

EMBODIMENT NO. 3

The liquid crystal molecules on the orientation film are controlled in that a longitudinal axis of a bar-shaped liquid crystal molecule is arranged parallel to a polymer chain of the orientation film. Then, the liquid crystal molecule is oriented having a tilted angle of approximately 5°–10° (pre-tilted) against the surface of the orientation film. This tilted angle is called a pre-tilt angle, which greatly gives effect on a rising-edge speed of the liquid crystal molecules in the liquid crystal display (LCD) at the time of the electric field being applied thereto and a rising-edge threshold value, so that the pre-tilt angle is considered to be an important factor in view of a response speed and an image quality.

The pre-tilt angle is considered to be caused by the fact that the polymer chain is arranged in the tilted manner against the surface of the orientation film. Therefore, it will be necessary to measure the tilted angle of the polymer chain against the film surface, in the course of evaluating the orientation film. However, the tilted angle of the polymer chain with respect to the orientation film is not evaluated by the infrared dichroic difference technique adopted in the first embodiment. In view of the fact, the third embodiment is made to further properly evaluate the rubbing-performed orientation film.

Figure 5:
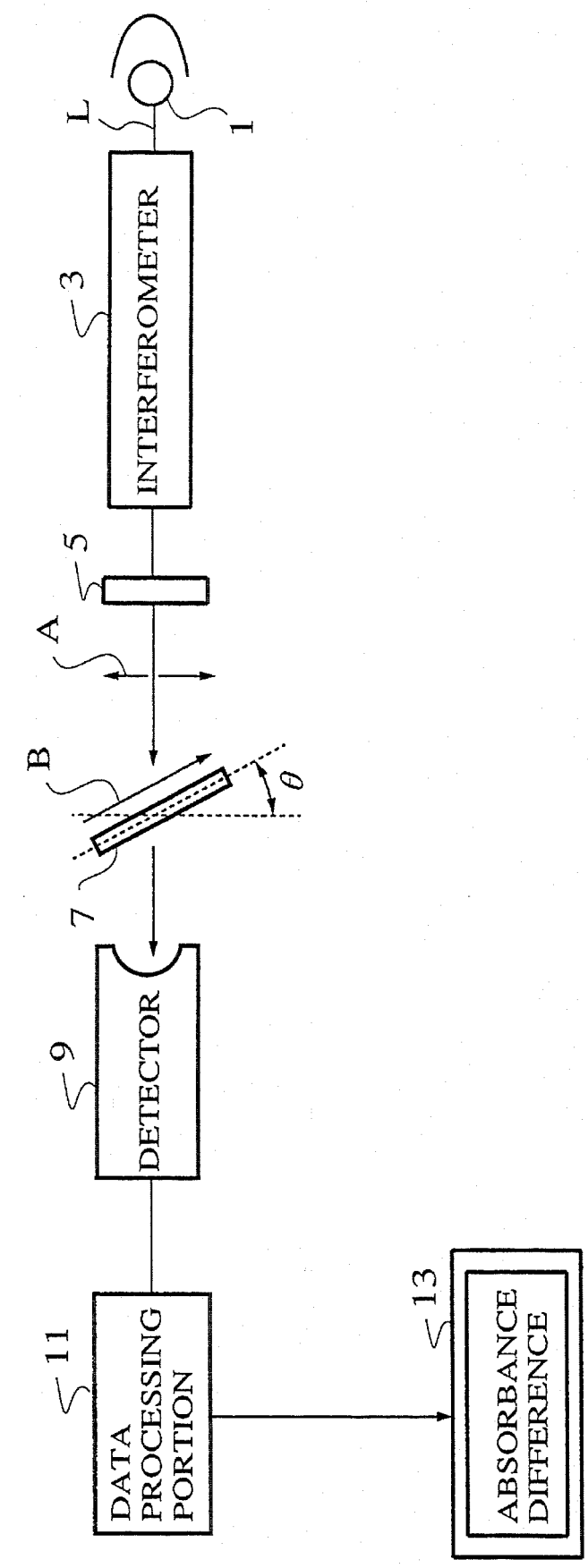
FIG. 5 is a block diagram showing a liquid crystal orientation film evaluating apparatus according to the third embodiment.

FIG. 5 is a block diagram showing a liquid crystal orientation film evaluating apparatus according to the third embodiment.

Referring to FIG. 5, along an optical axis of an infrared light source 1 for infrared light L, there are provided an interferometer 3, a polarizer 5, an orientation film sample 7 and a detector 9. A data processing portion 11 is connected to the detector so that detection data outputted from this detector 9 are data-processed in the data processing portion 11 so as to obtain an absorbance difference 13.

Figure 6:
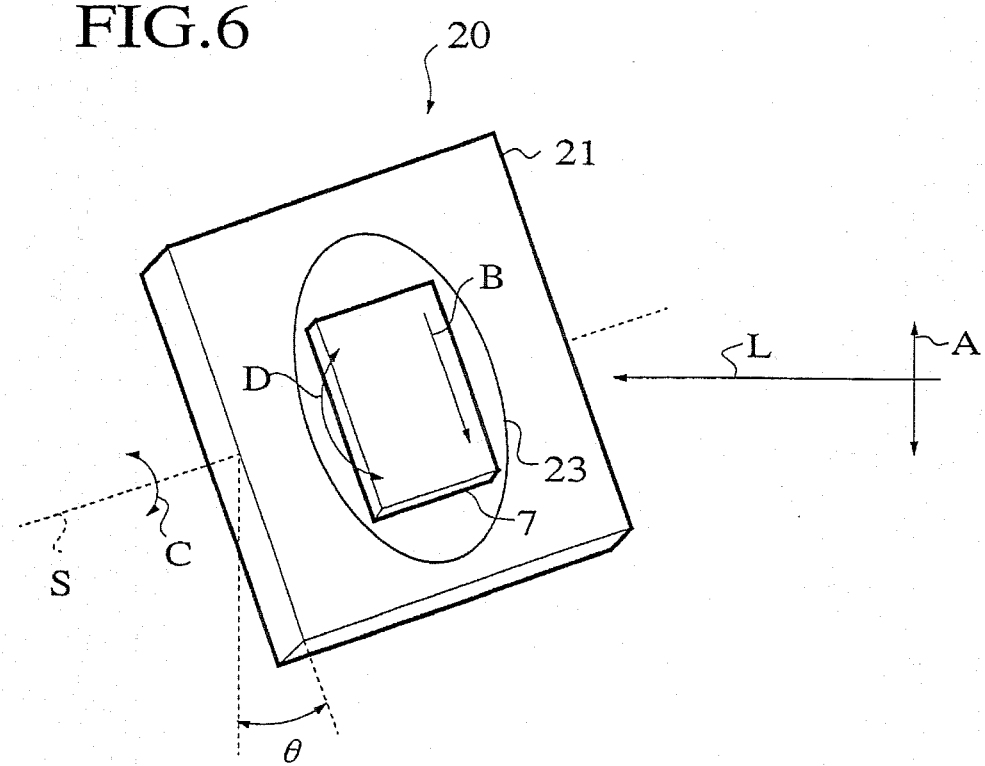
FIG. 6 is a perspective view showing a measurement tool utilized for the liquid crystal orientation film evaluating apparatus according to the third embodiment.

FIG. 6 is a perspective view showing a measurement tool utilized for the liquid crystal orientation film evaluating apparatus according to the third embodiment. With reference to FIG. 6, the orientation film sample 7 is fixed by a sample tool 20 so that the orientation film sample 7 is freely rotatable within a plane including the orientation film surface of the orientation film sample 7.

This sample tool 20 has a circular-shaped rotary plate 23 in its central portion. The rotary plate 23 is supported by a substrate 21 so that the rotary plate 23 is freely rotatable within a plane including a rotating surface thereof. The substrate 21 is freely rotatably constructed with a sample tilting axis S being a rotation axis. The sample tilting axis S and the rotary plate 23 are driven by respective motors (not shown) so that the rotation amount therefor is precisely controlled.

Thereby, the infrared light L which is in a polarized state parallel to the plane formed by the rubbing direction B of the orientation film sample 7 and the direction normal to the sample surface can be entered at a various angle ($-90° \leq \theta \leq +90°$) from the direction normal to the sample surface. Then, the absorbance of thus entered and transmitted light, or the absorbance difference at incident angles ($+\theta$ and $-\theta$) is measured.

When measuring the alignment degree for the orientation film, the measurement is preferably carried out at a characteristic absorption wavelength for the orientation film serving as the sample or dummy. The absorbance difference can be measured by the light having thus measured wave number that is usually a light in the infrared range.

In this embodiment, the polyimide resin is utilized for the orientation film 73a, 73b and is formed on a silicon substrate. After this orientation film 73 is orientation-processed by a rubbing machine, the orientation is measured by infrared spectrometer. The infrared light L emanated from the infrared light source 1 passes through the Michelson interferometer 3 that is a Fourier transform infrared spectrometer and the polarizer 5, and is entered to the orientation film substrate 7 at the incident angles of −50° to +50°.

Referring to FIG. 6, the direction A of the linearly polarized light on the sample surface is parallel to the rubbing direction B. The sample placed on the sample surface is tilted with respect to the axis orthogonal to the rubbing direction B.

Figure 7:
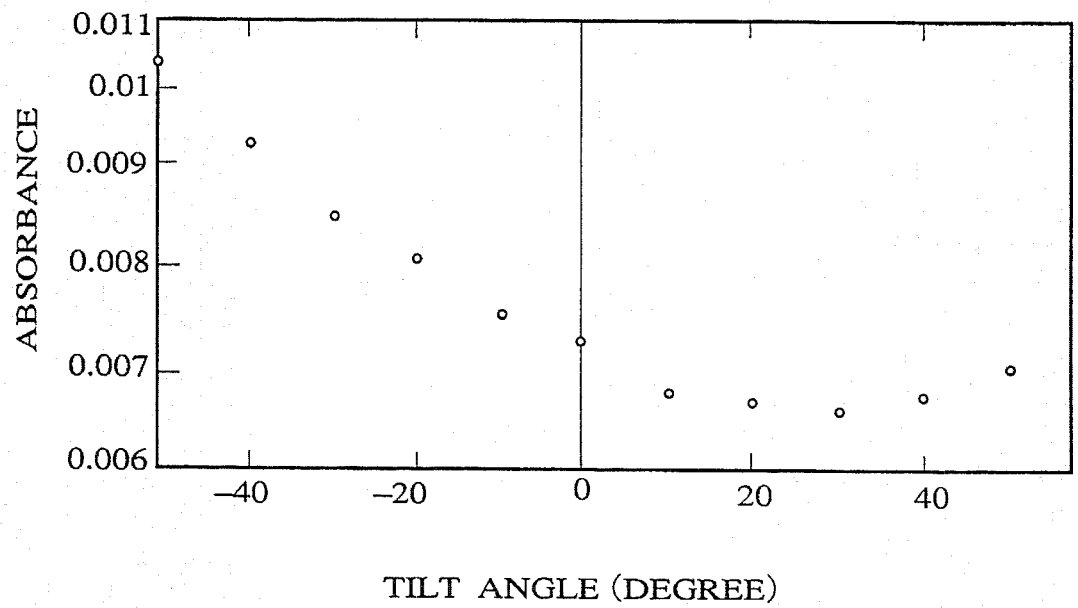
FIG. 7 is a graph showing correlation between the incident angle of infrared L and the infrared absorbance.

FIG. 7 is a graph showing correlation between the incident angle of infrared L and the infrared absorbance. This relationship can be explained by effects by which the path length of the infrared light through the polyimide orientation film is increased by tilting the sample, and by which the polyimide molecules are oriented having a wave angle against the sample substrate.

Thereby, by tilting the sample and measuring the infrared absorption thereof, a wave angle of the polyimide molecule and the surface of the sample substrate 71 can be detected. In order to actually manage the rubbing condition for the polymer film, a value of the infrared absorbance difference is calculated in two different sample tilting angles (preferably +50° and −50°) so as to monitor and manage this value. For its measurement, referring to FIG. 6, the orientation film substrate 7 is fixed on to the tool 20 having a predetermined angle, and after the infrared absorbance is measured, only the sample substrate 7 is rotated for 180° without changing the angle of the tool 20 against the infrared L so as to measure the infrared absorbance. In the above manner, the angle of the sample substrate with respect to an infrared light path is kept at a predetermined ± angle for a measurement purpose.

Figure 8:
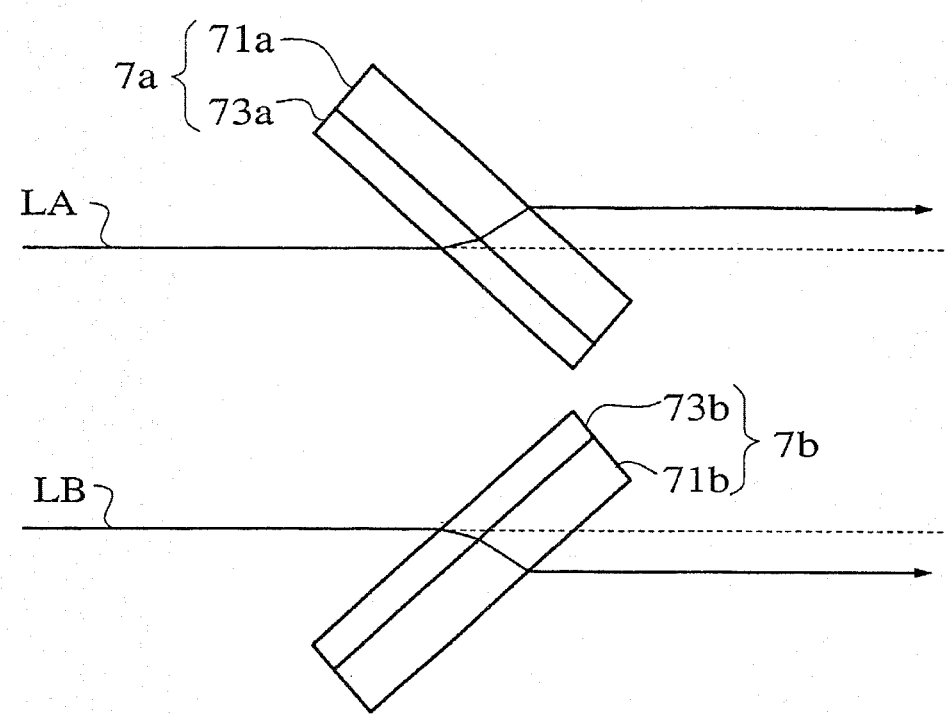
FIG. 8 illustrates a deviation of the infrared light path caused by the refraction.

A reason why the measurement is carried out in the above-described manner is that the infrared light path is deviated when the substrate angle with respect to the infrared light is changed due to refraction caused by sample substrates 71a, 71b as shown in FIG. 8. When the infrared light path is shifted, a position entering to the detector 9 is also deviated, so that a sensitivity therefor is also changed.

The measurement is performed by an FT-IR (Fourier transform Infrared spectometer), and the absorbance of a specific polymer absorption wavelength in its spectrum. Alternatively, as a simpler and faster technique, the specific polymer absorption wavelength alone may be monitored by utilizing a spectroscopic means such as a filter or grating or a homogeneous light source such as a laser.

EMBODIMENT NO. 3-1

Figure 9:
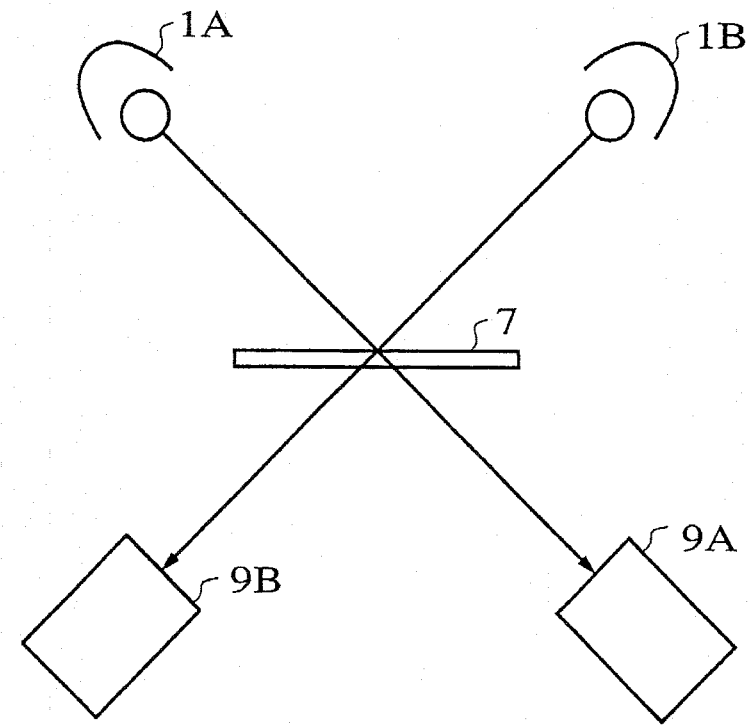
FIG. 9 is a block diagram showing a brief configuration for the liquid crystal orientation film evaluating apparatus according to the variation for the third embodiment.

Referring to FIG. 9, a variation for the third embodiment will be described. FIG. 9 is a block diagram showing a brief configuration for the liquid crystal orientation film evaluating apparatus according to the variation for the third embodiment.

In order to further simplify and make faster the measurement in the third embodiment, it will be effective to perform the measurement by utilizing two or more infrared beams as shown in FIG. 9. Referring to FIG. 9, infrared lights L emanated from a plurality of infrared light sources such as 1A, 1B are entered to the orientation film sample 7 at desired angles, and there are provided detectors 9A, 9B corresponding to the transmitted lights therefrom, respectively. Thereby, the measurement is simultaneously realized at various plurality of infrared incident angles. According to this variation for the third embodiment, there would be no need to take measurements by rotating the sample, and the number of measurement will be one, thus realizing a faster and simpler measurement. Care shall be taken to precisely adjust the detectors 9A, 9B for there may be a case where the sensitivity for the detectors 9A and 9B is different from other.

EMBODIMENT NO. 3-2

Figure 10:
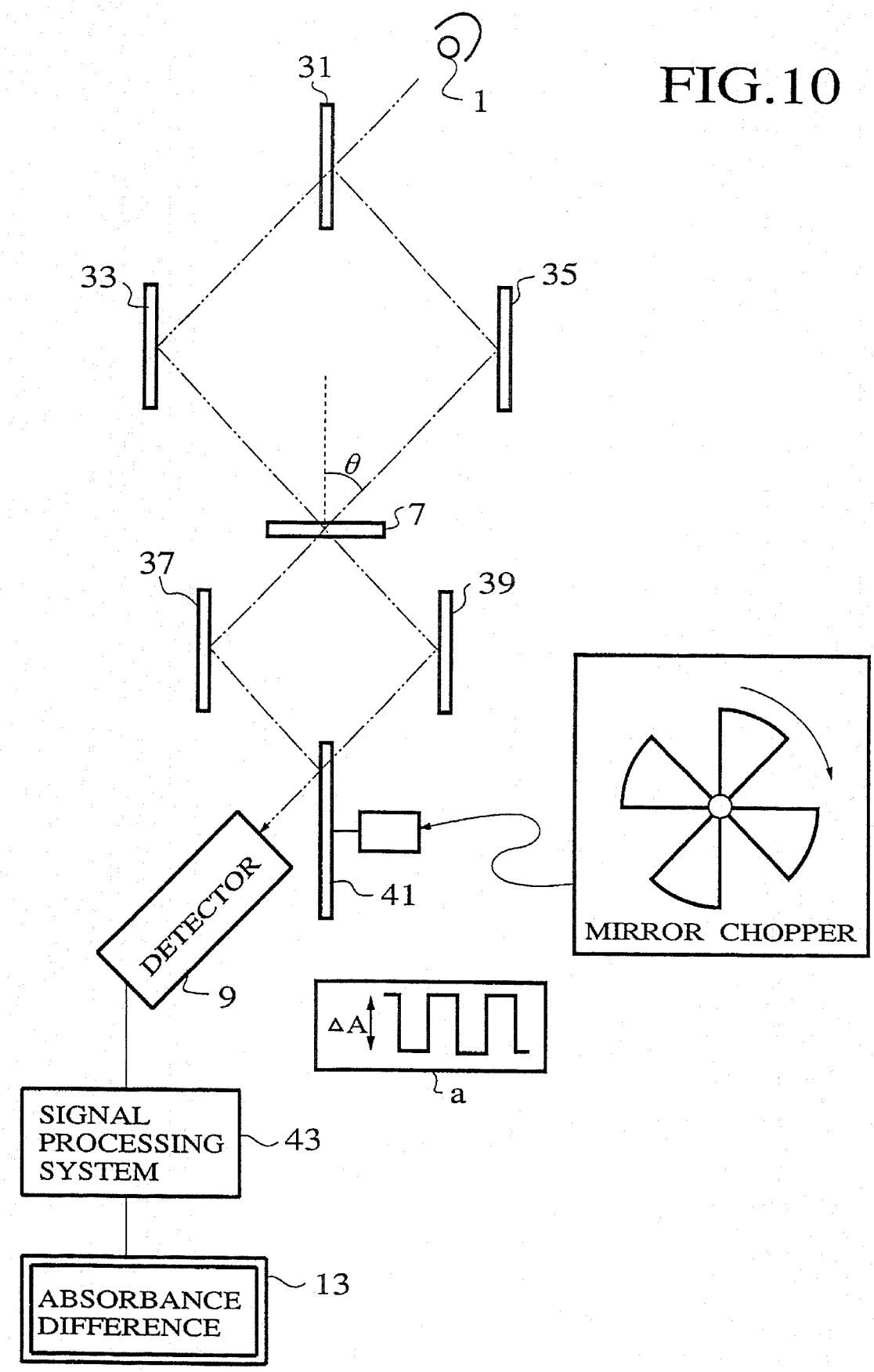
FIG. 10 is a block diagram showing another brief configuration for the liquid crystal orientation film evaluating apparatus according to another variation for the third embodiment.

Referring to FIG. 10, another variation for the third embodiment will be described. FIG. 10 is a block diagram showing another brief configuration for the liquid crystal orientation film evaluating apparatus according to another variation for the third embodiment.

In this another variation for the third embodiment, the measurement is possible by utilizing a single infrared light source and a single detector therefor. That is, without using a plurality of detectors as in above variation, the measurement is carried out simultaneously at two different infrared incident angles, so as to output the difference therebetween. A structure therefor will be described below with reference to FIG. 10.

Referring to FIG. 10, the infrared light L emanated from the infrared light source 1 is divided to two different light paths by means of a half mirror 81 (the two light paths being indicated with one having two dots between the line and with other having a dot between the line in FIG. 10). After the divided light paths are reflected by a mirror 88 and a mirror 85, the two reflected infrared lights are intersected at a point on the orientation film 78 of the orientation film sample 7, and then are transmitted through this orientation film sample 7. Then, the two lights are entered to and transmitted through the orientation film sample 7 at incident angles of +θ and −θ, respectively. After thus transmitted infrared lights L are again reflected by a mirror 37 and a mirror 39, respectively, the reflected lights enter to a mirror chopper 41.

In the mirror chopper 41, four fan-shaped blades have each an arc equivalent to one eighth of a circumference and are rotated at a predetermined speed. The four fan-shaped blades lie on the same plane and are made of material such as a mirror which optically has total reflectivity for the light including the infrared. By rotating the blades of the mirror chopper 41, the infrared L reflected by the mirror 37 is reflected by the blade of the mirror chopper 41, whereas another infrared L reflected by the mirror 39 is passed between the blades. Thereby, the two distinct infrared lights are arrived at the detector 9, alternately. A detection signal a from the detector 9 is processed by a signal processing system 43 synchronized with the mirror chopper 41 such as the lock-in amplifier, so that the difference alone is output. Accordingly, the absorbance difference in terms of two different incident angles is measured at a high speed so as to control optimally the rubbing conditions for the orientation film.

EMBODIMENT NO. 4

The first embodiment and third embodiment will enhance advantageousness of present invention by combining each with the fourth embodiment which presents a novel feature in a rubbing processing technique, thereby, the orientation state is further precisely controlled so as to obtain the stable production condition and increase the productivity and yield for producing the liquid crystal orientation film.

Figure 11:
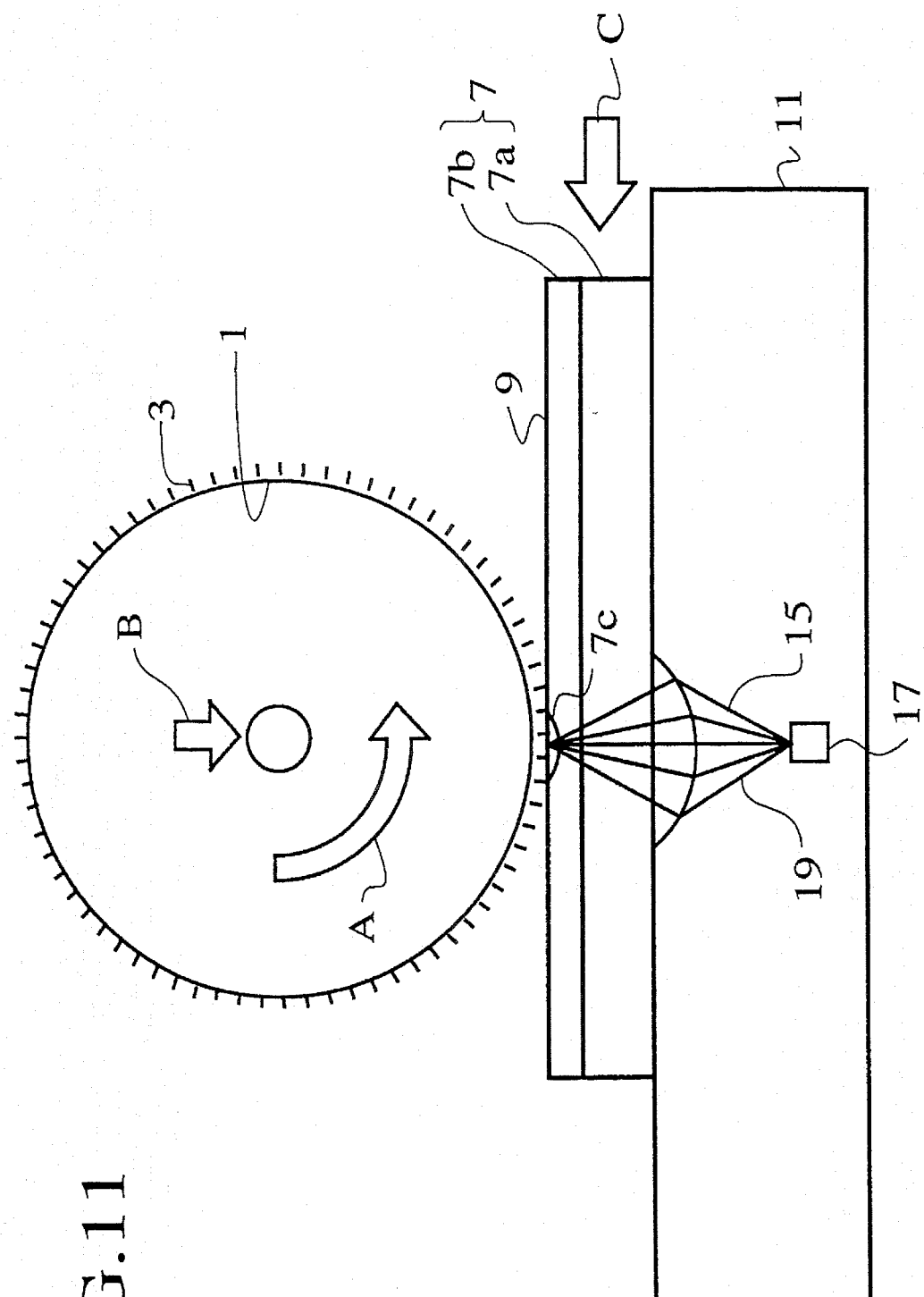
FIG. 11 is a cross sectional view of a rubbing processing apparatus according to the fourth embodiment, viewed from a side thereof.
Figure 12:
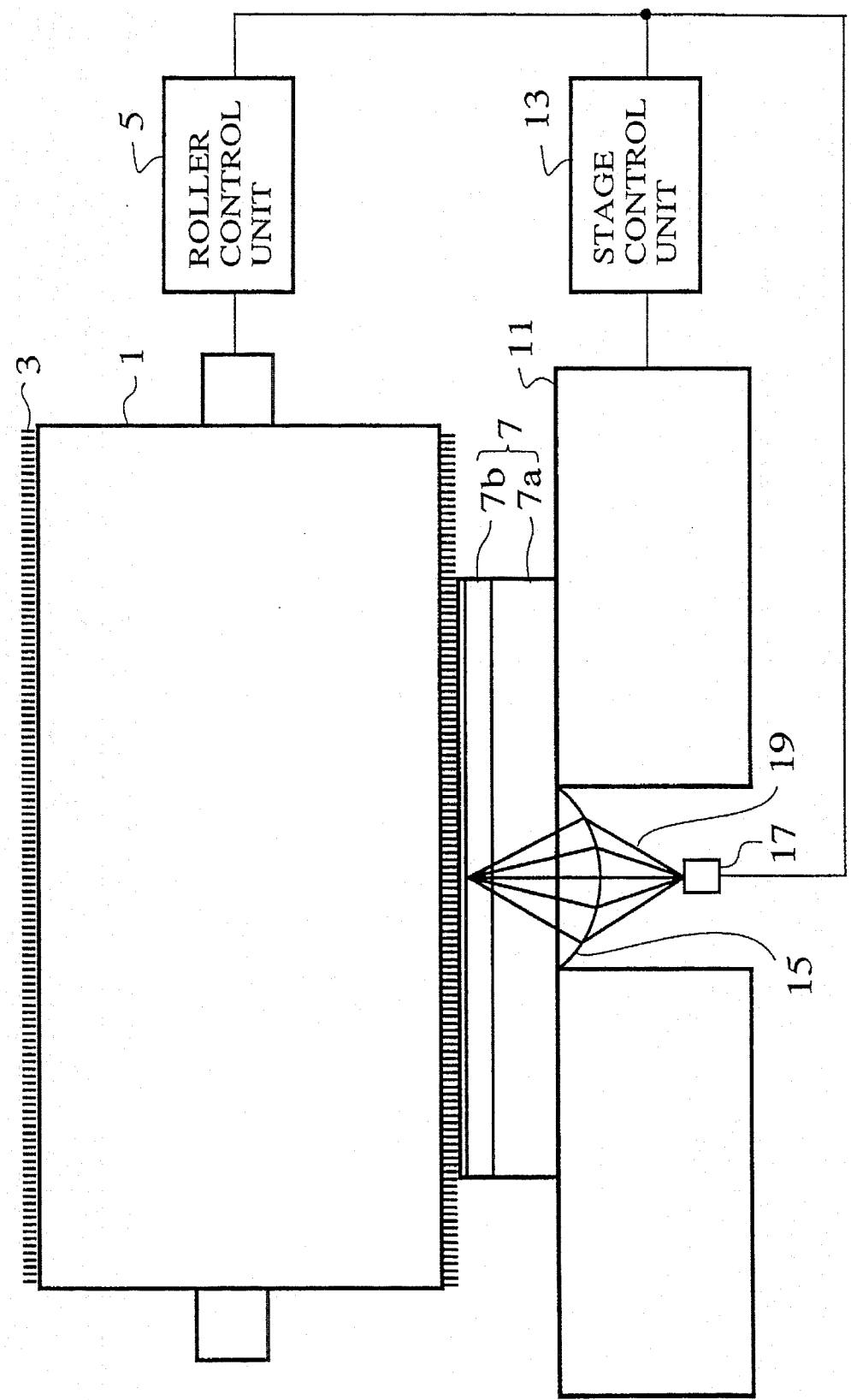
FIG. 12 is a cross sectional view of the rubbing processing apparatus shown in FIG. 11, viewed from the top thereof.

FIG. 11 is a cross sectional view of a rubbing processing apparatus according to the fourth embodiment, viewed from a side thereof. FIG. 12 is a cross sectional view of the rubbing processing apparatus shown in FIG. 11, viewed from the top thereof.

Referring to FIG. 11 and FIG. 12, the rubbing apparatus according to the fourth embodiment, comprises a rubbing roller portion and a stage portion. The rubing roller portion comprises: a rubbing roller 1; a rubbing cloth S wounded around an outer circumference of the rubbing roller 1; a drive portion (not shown) which rotates the rubbing roller 1 in a roller rotation direction indicated with an arrow mark A as well as moves the rubbing roller 1 in the vertical direction indicated with B; and a roller control portion 5 which controls a rotation speed and a position of the rubbing roller 1 by controlling the driver portion.

The stage portion comprises: a stage 11 disposed counter to the rubbing roller 1 at a predetermined clearance from the rubbing roller 1; a stage control portion 13 which controls a transport mechanism (not shown) that translates the orientation film substrate 7 provided on the stage 11 in a unidirection with the orientation film substrate 7 being held horizontally; an infrared condensing lens 15 provided in an opening portion that is cylindrically opened between the stages 11, 11 and is disposed counter to the rubbing roller 1; an infrared detector 17 which detects infrared beam 19 that is condensed by the infrared condensing lens 15 and that is introduced within the stage 11.

As the orientation film substrate 7, there is used a polyimide film 7b (orientation film) that is coated on a glass substrate 7a with ITO.

Next, the operation for above-described structure according to the fourth embodiment will be described below.

First, the orientation film substrate 7 is placed on a predetermined position of the stage 11. The stage control portion 13 drives and controls the transport mechanism so that the orientation film substrate 7 provided on the stage 11 is translated under the rubbing roller 1 at a predetermined traslating speed. Then, the rotation speed and position of the rubbing roller 1 are controlled by the roller control portion 5 so that the orientation film substrate 7 comes in contact with the rubbing cloth 3 wounded around the rubbing roller 1, at a central part of the stage 11, so as to perform the rubbing operation. By frictional heat generated from the rubbing opepration, the polyimide film 7b is alignment-processed.

The surface temperature of the orientation film substrate 7 placed on the stage 11 is measured in a manner that the infrared beam 19 caused by the frictional heat due to the polyimide film 7b and the rubbing cloth 3 is condensed to the infrared detector 17 by the infrared condensing lens 15. An output of the measured temperature is sent to the roller control portion 5 and the stage control portion 13 by which the rubbing state is controlled and changed if necessary.

In other words, the frictional heat generated is controlled and the temperature of the frictional surface of the polyimide film 7b is controlled by changing at least one of factors among the rotation speed of the rubbing roller 1, a depression pressure of the rubbing roller 1 and the translating speed of the stage 11. Moreover, the above-mentioned temperature control is affected by other factors such as the temperature, moisture, air flow rate in an atmosphere where the rubbing processing apparatus is placed, and whethere or not there is provided a heater and whether or not there is provided a fan or fin for cooling purpose. Thus, these other factors are preferably controlled to be stable by means of air conditioning or the like.

The polyimide film 7b to which the temperature control is performed by the above infrared detector 17 and the rubbing process is performed, is examined for its molecular orientation degree by a polarized dichroic measurement. As a result thereof, a value of the dicroic difference therefor is improved approximately by a factor of 2 compared to the polyimide film to which the temperature control is not performed.

Figure 13:
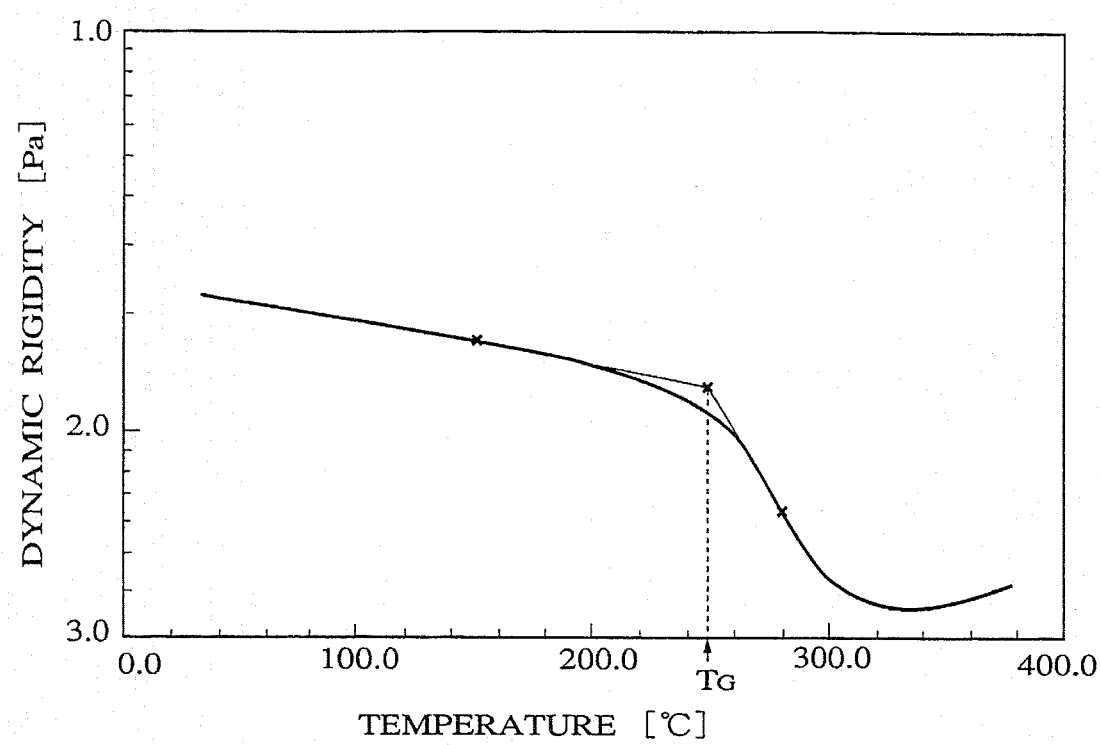
FIG. 13 is a graph showing a temperature dependency of dynamic modulus in the polyimide film, related to the fourth embodiment.

Referring to FIG. 13, a temperature dependency of dynamic modulus in the polyimide film will be described below.

With reference to FIG. 13, the polyimide film is rapidly softened beyond its glass transition point. Beyond the increase of more than 60° from the glass transition point, the alignment effect due to the softening of the polyimide is not improved. Then, the time duration required for the polyimide to become cooled and hardened is increased, so that the once-aligned polyimide will return to the original condition of no orientation during this prolonged cooling and hardening period, thus the alignment efficiency being deteriorated.

Then, in order to examine the orientation degree of the polyimide film, the infrared dichroic difference is measured utilizing the polarized light. As a result, the infrared dichroic difference is 0.0055 when the polyimide film is cooled by a cooling rate of 180°/sec, and a sufficient orientation of polyimide film is obtained. When measured below the cooling rate of 160°/sec such as 120°/sec, the dichroic difference shows a low value (0.0010 at the cooling rate of 120°/sec) and the orientation barely occurred.

As for cooling immediately after the frictional operation of the polyimide film, air cooling may be performed when the frictional temperature under rubbing operation is no so high. Moreover, the rubbing efficiency can be improved in a manner that the atmospheric temperature is lowered and the cooling is performed from a substrate side, or a cooling gas is blowed thereto.

As described above, by implementing the fourth embodiment, the orientation state of the orientation film is precisely controlled, so that a stable production condition can be obtained. Thereby, the productivity and production yield therefor are improved, so that economically priced liquid crystal display units having highly precise image quality can be supplied.

In summary, the orientation state of the orientation film surface is precisely and accurately controlled in accordance with the temperature of the surface of the polymer orientation film.

MODIFICATION

In order to further improve the first and second embodiments, following modified versions are also suggested.

In the event that the finished product (patterning-performed commercial commodity) uses a glass substrate, the infrared light is very much absorbed by the glass. Moreover, in the event that there exists a pattern of a transparent electrode, an accurate measurement based on the infrared dichroic difference may not be carried out due to the effect of the pattern on the infrared dichroic property. In other words, the angles of the two linearly polarized lights with respect to the transparent electrode become asymmetric, so that the infrared reflected by the transparent electrode differs at each polarization. Thus, the measurement of difference therebetween will not be reliable since the unwanted signals may be stronger than signals corresponding to the wanted information on the molecular orientation obtained from the infrared dichroic difference.

(Modification No. 1)

Figure 14:
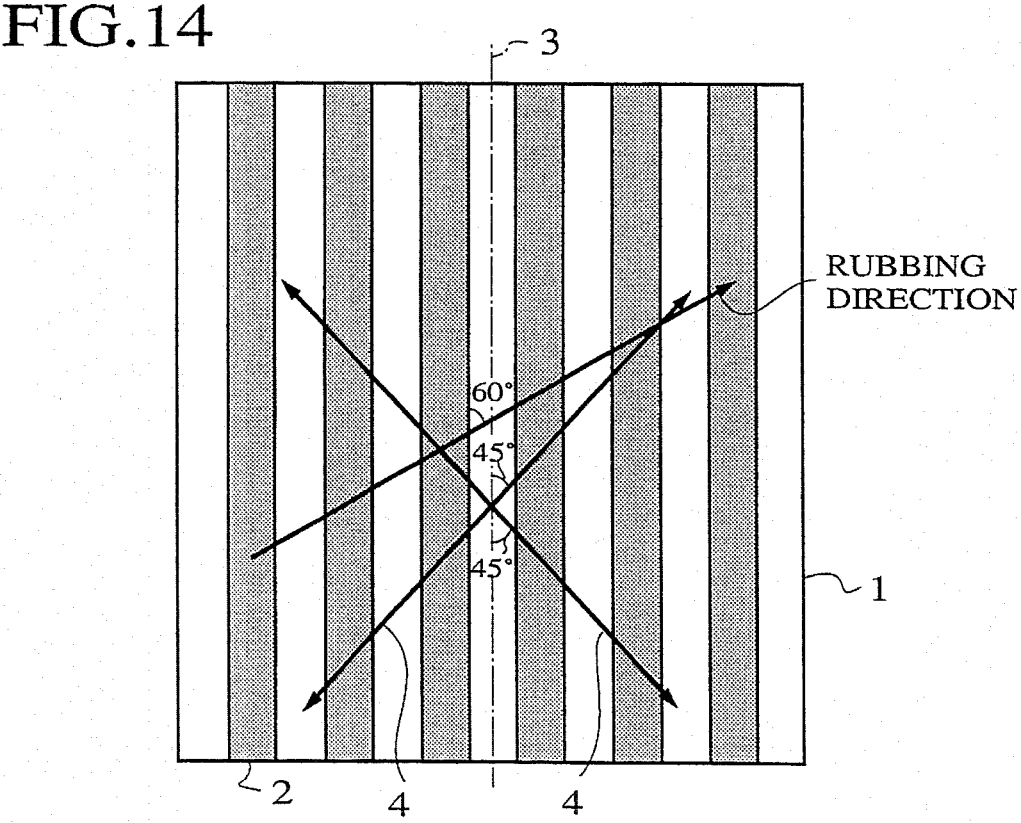
FIG. 14 shows the surface of the orientation film substrate according to the first modification for the first and second embodiments.

FIG. 14 shows the surface of the orientation film substrate according to the first modification for the first and second embodiments.

Referring to FIG. 14, the orientation film such as polyimide resin is formed on a glass substrate 1 with the transparent electrode such as ITO, and is rubbing-processed. A pattern 2 of the ITO transparent electrode is, for example, of a stripe shape. In order to be point-symmetric with respect to a symmetry axis 3 of the pattern 2, two linearly polarized lights having angles of ±45° on the orientation film surface are utilized so as to perform the infrared spectrum measurement.

Figure 15:
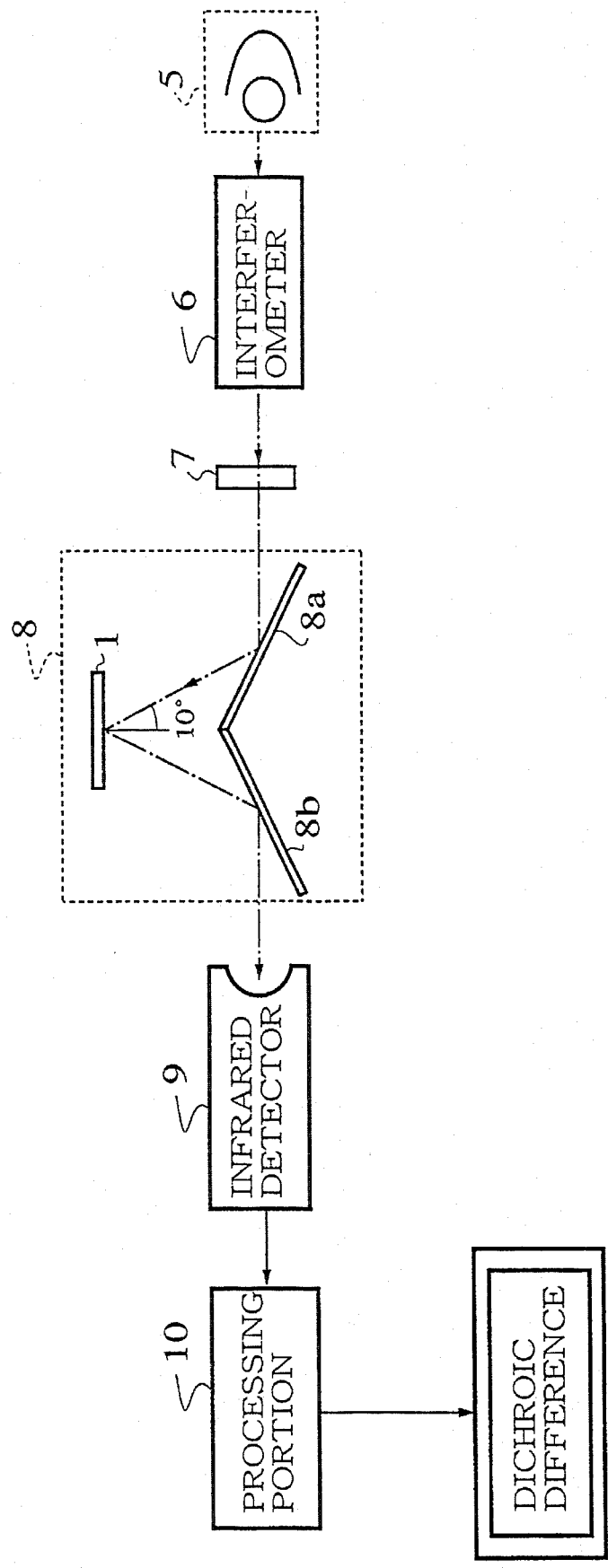
FIG. 15 shows a measuring system for this first modification.

FIG. 15 shows a measuring system for this modification. Along an optical axis of an infrared light source 5, there are provided a Michelson interferometer 6, a polarizer 7, reflection measuring units 8a, 8b, and an infrared detector 9. The signal outputted from the infrared detector is fed to a processing portion 10 so as to output the infrared dichroic difference signals therefrom. The measurement is carried out with the polarization of the infrared being fixed at s-polarization so that the polarization is at ±45° with respect to the symmetry axis of the transparent electrode pattern by rotating the sample substrate. In other words, the polarization of the infrared is fixed at the direction which is orthogonal to the incident plane (a plane in which the incident light and reflected light pass (s-polarization).

Figure 16:
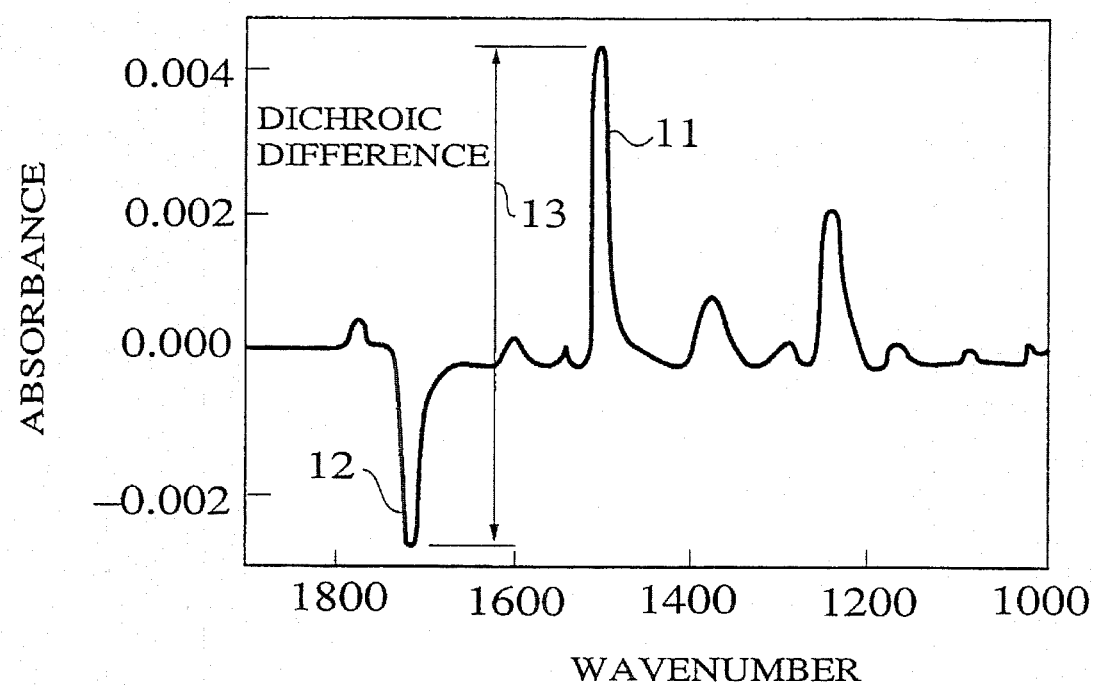
FIG. 16 is a graph showing the dichroic difference.

The incident angle of the infrared is preferably close to the vertical incidence, and is set to approximately 10°, for example. When absorbance difference of the above measurement by the two polarizing directions, there is obtained spectrum as shown in FIG. 15. Referring to FIG. 16, a peak 11 at approximately 1500 $cm^{-1}$ accounts for a benzene-ring skeleton vibration of the polyimide molecule, whereas another peak 12 at approximately 1720 $cm^{-1}$ accounts for the stretching vibration of carbonyl group attached to an imide ring. The difference, 13, of height of the two peaks are taken so as to be output as a dichroic difference value. In this case, notice that the dichroic difference is taken as a peak-to-peak difference.

The "s" in the s-polarized light indicates "senkrecht" meaning vertical, "p" in p-polarized light indicates "parallel" meaning parallel.

(Modification No. 2)

This second modification is similar to the second embodiment.

Refer to FIG. 1 as well as FIG. 15. There may be utilized a photoelastic modulator so that the measurement can be carried out without rotating the orientation film. The photoelastic modulator can switch the two linearly polarized lights at a high speed, so that the absorbance difference of the two lights at almost simultaneous time can be obtained. As a result, the influence due to the water vapor and carbon dioxide in the atmosphere can be eliminated. In this case, there are provided the photoelastic modulator 14 immediately after the polarizer 7 (see also FIG. 1). The signal from the detector is connected to a lock-in amplifier, and is output to the processing portion 10 after the modulation by the photoelastic modulator is set free.

Figure 17:
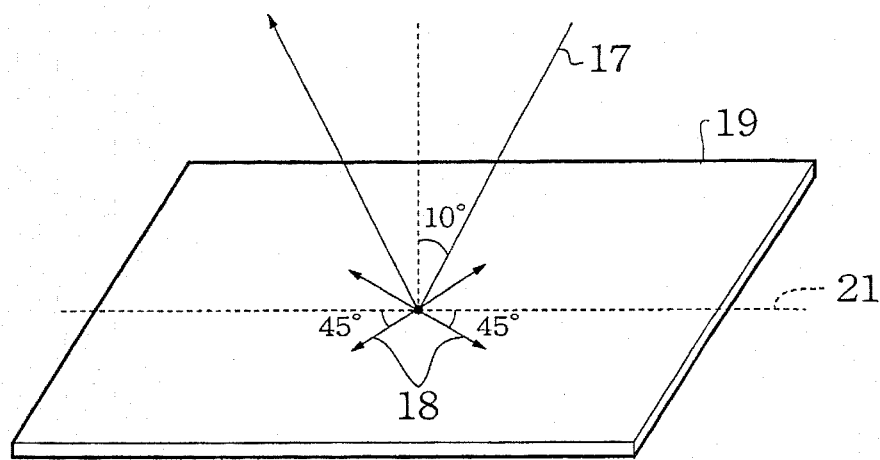
FIG. 17 illustrates polarized lights and the orientation film substrate according to the second modification for the first and second embodiments.

The lock-in amplifier and the photoelastic modulator are sychronously controlled by a controller. Referring to FIG. 17, the measurement is carried out with the incident angle of infrared 17 being 10°, and the direction 18 of the linearly polarized light is set at 45° with respect to the incidence plane (a plane in which the incidence light and reflected light paths pass). Thereby, the angles ±45° is symmetric with respect to a mirror in the measuring system, so that the difference in the reflection factor due to the polarization characteristic can be eliminated. Then, it is necessary to set to an angle by doing a fine adjustment for the polarizing direction so that the polarization characteristic is not present.

Accordingly, thus adjusted two linearly polarized lights 18 (each of which is orthogonal to other) become symmetric with respect to the symmetry axis 21 of the ITO transparent electrode pattern of the orientation film substrate 19. Namely, the orientation film substrate 19 is set so that the linearly polarized lights are at ±45° as described above. The output of the lock-in amplifier 15 is indicated as the infrared absorbance difference of the two polarized lights. Thus, its spectrum is obtained as the dichroic difference value, similar to the case in the first modification. Moreover, as described in the second embodiment, the measurement system can be implemented to the production line of the liquid crystal display devices, so that there may be provided an optical system in the production line set up after the rubbing processing is finished.

(Modification No. 3)

Figure 19:
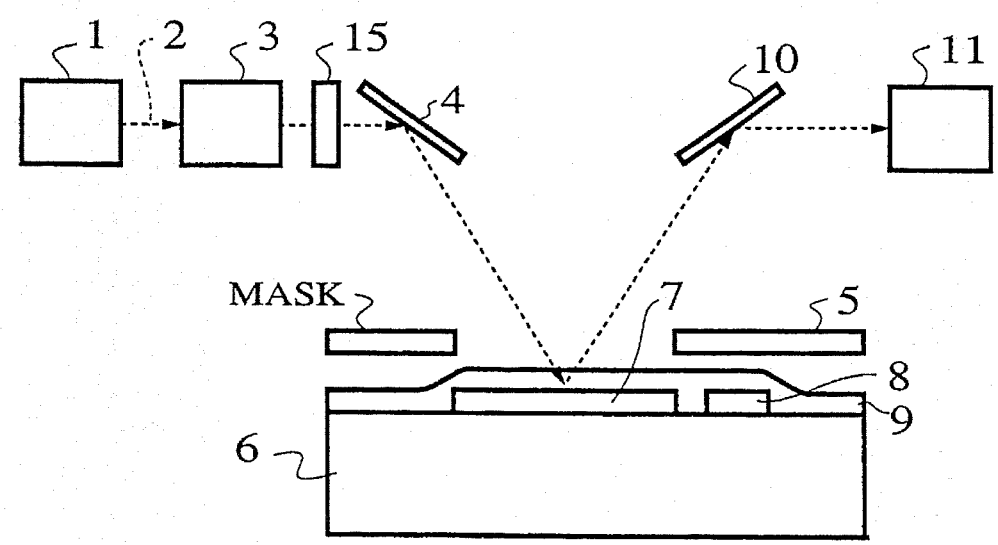
FIG. 18 and FIG. 19 illustrate the third modification for the first and second embodiment.
Figure 18:
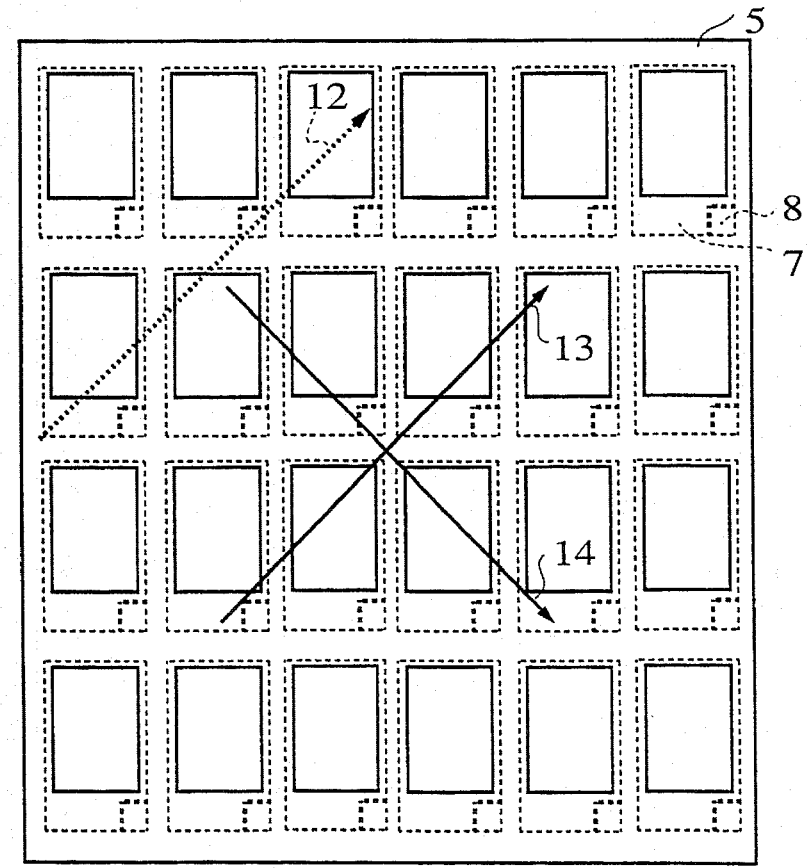

Similar to the above first and second modifications, following third and fourth modifications are made to further improve the first and second embodiments in order to eliminate or offset the anisotropy of the reflected light caused by the pattern formed on the orientation film substrate. In other words, on the liquid crystal display substrate there are formed patterns composed of TFT (Thin Film Transistor), a black matrix or an electrode. Thereby, the reflectance spectrum of the light is greatly influenced by the patterns. Thus, the anisotropy due to the patterns on the substrate forms a large background in the event that measurement for the reflection and absorption is carried out by rotating the substrate in order to measure the dichroic difference of the orientation film on the substrate, thus the sensitivity for the dichroic difference measurement being greatly deteriorated. Therefore, in this modification, such a pattern is masked by a masking means. This is illustrated in FIG. 18 and FIG. 19. In FIG. 19, the reference numeral 8 indicates the TFT. FIG. 18 shows a top view of the sample substrate 6 and the mask 5. The masking pattern 5 has transparent openings corresponding to electrode patterns.

After the infrared light 2 emanated from the infrared light source 1 is transmitted through the interferometer 3 and the polarizer 15, it is reflected by a mirror 4 and is transmitted through a mask substrate 5 and is radiated to the liquid crystal display substrate 6 with the S polarization state. The incidence of the infrared light occurs from directions parallel 13 to and vertical 14 to the rubbing direction 12, and is entered alternately by rotating the substrate 6 at 90°. The infrared light radiated to the substrate 6 is reflected by the transparent electrode surface 7, while it is being absorbed somehow by the orientation film 9 on the liquid crystal display substrate 6. The reflected light is entered to the infrared light detector 11 by reflected by a mirror 10 so as to be detected, after transmitted through the mask 5.

A shape of the mask placed on the substrate is such that it has a mirror symmetry. By placing the mask, the pattern that plays a role to lose the mirror symmetry is masked out.

Material of the masks are preferably the material that absorbs the infrared light such as a carbon, in order to avoid stray light and interference of the infrared light. The position of the masks may be anywhere in the light path of the infrared light.

(Modification No. 4)

As for another variation for the above third modification, the fourth modification will be described.

After the infrared light 2 emanated from the infrared light source 1 is transmitted through the interferometer 3 and the polarizer 15, it is reflected by a mirror 4 and is transmitted through a mask substrate 5 and is radiated to the liquid crystal display substrate 6 with the s-polarization state. The incidence of the infrared light is by directions parallel to and vertical to the rubbing direction, and is entered alternately by rotating the substrate 6 by 90°. The infrared light radiated to the substrate 6 is reflected by the transparent electrode surface 7, while it is being absorbed somehow by the orientation film 9 on the liquid crystal display substrate 6.

The above measurement is performed before and after the 90° rotation, and the dichroic difference is measured from each absorbance. Then, the dichroic difference spectrum obtained before the rubbing operation is memorized in a computer. Then, the memorized dichroic difference spectrum obtained before the rubbing operation is subtracted from the dichroic difference spectrum obtained after the rubbing operation, so that a true dichroic difference spectrum due to the rubbing operation can be obtained. The number of rubbing operation and/or other factors in the rubbing apparatus are adjusted so that the intensity of this subtracted spectrum is constant and stable, thus being able to obtain a desired rubbing strength.

Besides those already mentioned above, many modifications and variations of the above embodiments may be made without departing from the novel and advantageous features of the present invention. Accordingly, all such modifications and variations are intended to be included within the scope of the appended claims.

What is claimed is:

1. An orientation film evaluating apparatus comprising:

means for radiating infrared light;

polarizing means for polarizing the radiated infrared light at varied angles to an orientation film formed on an electrode on a substrate, and for irradiating the polarized infrared light to the orientation film;

detection means for detecting infrared light passing through the orientation film and reflected by the electrode; and evaluating means for obtaining a difference of intensity of infrared light detected by the detection means with respect to the infrared light polarized in different directions, and for evaluating an orientation capability of the orientation film.

2. The apparatus of claim 1, wherein the polarizing means includes: coordinates shifting means by which two linearly polarized infrared lights make two angles symmetric to a symmetry axis of a transparent electrode pattern provided in an orientation film substrate.

3. The apparatus of claim 1, wherein a masking pattern is inserted to the orientation film at an incidence side or a reflection side, the masking pattern having a transparent opening corresponding to an electrode pattern.

4. The apparatus of claim 1, wherein the detection means includes a memory means for storing the absorbance difference obtained before and after a rubbing operation, and wherein the evaluating means includes a subtracting means for subtracting the absorbance difference obtained before the rubbing operation, from that obtained after the rubbing operation so as to eliminate an anisotropic background caused by a pattern provided on the orientation film substrate.

5. The apparatus of claim 1, wherein the orientation film is a liquid crystal orientation film.

6. An orientation film evaluating apparatus, comprising:

radiating means for radiating infrared light toward an orientation film sample which is processed in a uniaxial orientation;

irradiating means in which the infrared light which is in a polarized state parallel to a plane formed by a uniaxial-orientation direction of the orientation film sample and a direction normal to the surface of the orientation film sample enters the orientation film sample at various angles from the direction normal to the sample surface, at a characteristic absorption wavelength thereof;

detection means for detecting the infrared light transmitted through the orientation film sample; and evaluating means for evaluating the orientation film based on (1) a difference of intensities of the transmitted light corresponding to the infrared light irradiated from different directions and (2) said different directions.

7. The apparatus of claim 6, wherein the infrared light radiating means includes a plurality of infrared light sources at desired angles, and the detection means includes a plurality of detectors corresponding to the plurality of infrared light sources, so that measurement is simultaneously realized at various plurality of infrared incident angles.

8. The apparatus of claim 6, wherein there is provided a single infrared light source and there is provided a single detection means, and further comprising a measuring means including:

a half mirror which divides the radiated infrared light into two different light paths;

a first set of mirrors, each of which is disposed counter to the other, which reflect the divided light paths, respectively, so that the two reflected infrared lights are intersected at a point on the orientation film of the orientation film sample;

a second set of mirrors, each of which is disposed counter to the other, which reflect the divided infrared lights transmitted through the orientation film sample; and a mirror chopper to which the two divided infrared lights reflected by the second set of mirrors enter, the mirror chopper having an alternate means by which the two infrared lights arrive at the detector, alternately.

9. The apparatus of claim 8, wherein a detection signal from the detection means is processed by a lock-in amplifier synchronized with the mirror chopper.

10. A method for evaluating an orientation film, comprising the steps of:

radiating infrared light;

polarizing the radiated infrared light at varied angles to an orientation film formed on an electrode on a substrate;

irradiating the polarized infrared light to the orientation film;

detecting infrared light passing through the orientation film and reflected by the electrode;

obtaining a difference of intensity of infrared light detected by the detecting step with respect to the infrared light polarized in different directions; and evaluating an orientation capability of the orientation film based on said difference.

11. A method for evaluating an orientation film, comprising the steps of:

radiating infrared light toward an orientation film sample which is processed in a uniaxial orientation;

irradiating the infrared light which is in a polarized state parallel to a plane formed by a uniaxial-orientation direction of the orientation film sample and a direction normal to the surface of the orientation film sample so as to enter the orientation film sample at various angles from the direction normal to the sample surface, at a characteristic absorption wavelength thereof;

detecting the infrared light transmitted through the orientation film sample; and evaluating the orientation film based on (1) a difference of intensities of the transmitted light corresponding to the infrared light irradiated from different directions and (2) said different directions.

* * * * *